(12) United States Patent
Xuan et al.

(10) Patent No.: US 10,259,798 B2
(45) Date of Patent: Apr. 16, 2019

(54) HIGH-PURITY MAGNESIUM LITHOSPERMATE B AND PREPARATION METHOD THEREFOR

(71) Applicants: SHANGHAI INSTITUTE OF MATERIA MEDICA CHINESE ACADEMY OF SCIENCES, Shanghai (CN); SHANGHAI GREEN VALLEY PHARMACEUTICAL CO., LTD., Shanghai (CN)

(72) Inventors: Lijiang Xuan, Shanghai (CN); Yiping Wang, Shanghai (CN); Weibin Song, Shanghai (CN); Chunguang Chen, Shanghai (CN); Dingxiang Li, Shanghai (CN); Xiaoyu Zhou, Shanghai (CN); Yunlong Gu, Shanghai (CN); Liang Hu, Shanghai (CN); Jing Zhao, Shanghai (CN); Wenwei Xu, Shanghai (CN); Shumei Wang, Shanghai (CN)

(73) Assignees: SHANGHAI INSTITUTE OF MATERIA MEDICA CHINESE ACADEMY OF SCIENCES, Shanghai (CN); SHANGHAI GREEN VALLEY PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/301,265

(22) PCT Filed: Feb. 9, 2015

(86) PCT No.: PCT/CN2015/072539
§ 371 (c)(1),
(2) Date: Dec. 13, 2016

(87) PCT Pub. No.: WO2015/149589
PCT Pub. Date: Oct. 8, 2015

(65) Prior Publication Data
US 2017/0137399 A1  May 18, 2017

(30) Foreign Application Priority Data
Apr. 1, 2014  (CN) .......................... 2014 1 0137310

(51) Int. Cl.
*A61K 36/00* (2006.01)
*C07D 307/86* (2006.01)
*A61K 31/343* (2006.01)
*A61K 36/537* (2006.01)

(52) U.S. Cl.
CPC .......... *C07D 307/86* (2013.01); *A61K 31/343* (2013.01); *A61K 36/537* (2013.01)

(58) Field of Classification Search
CPC .................................................... A61K 36/00
See application file for complete search history.

(56) References Cited

U.S. PATENT DOCUMENTS

2010/0048618 A1* 2/2010 Chan .................... C07D 405/14
                                                        514/308
2010/0174097 A1   7/2010 Jung et al.

FOREIGN PATENT DOCUMENTS

CN       102058599 A   *  5/2011
CN       102204955 A   * 10/2011

OTHER PUBLICATIONS

International Preliminary Report on Patentability of PCT/CN2015/072539 mailed from the International Bureau of WIPO dated Oct. 13, 2016.
Written Opinion of the International Searching Authority of PCT/CN2015/072539 dated May 15, 2015.
International Search Report of the International Searching Authority dated May 15, 2015 in PCT/CN2015/072539.

* cited by examiner

*Primary Examiner* — Qiuwen Mi
(74) *Attorney, Agent, or Firm* — Womble Bond Dickinson (US) LLP; Cristin H. Cowles; Sai Seetharaman

(57) ABSTRACT

The present invention relates to a method for preparing magnesium lithospermate B. The method is characterized in that: magnesium lithospermate B is extracted or purified from a *Salvia miltiorrhiza* plant material or a *Salvia miltiorrhiza* extract in the presence of an added magnesium salt. The present invention also relates to a high-purity magnesium lithospermate B product prepared by the method of the present invention, wherein the content of magnesium lithospermate B is more than 95% by weight.

11 Claims, 3 Drawing Sheets

HIGH-PURITY MAGNESIUM LITHOSPERMATE B AND PREPARATION METHOD THEREFOR

TECHNICAL FIELD

The present invention relates to a method for preparing high purity magnesium lithospermate B and high purity magnesium lithospermate B prepared therefrom.

TECHNICAL BACKGROUND

Salvianolates are the water-soluble active components of *Salvia miltiorrhiza*, and have been widely used clinically thanks to their significant biological activities such as anti-oxidation, anti-platelet aggregation and anti-atherosclerosis. Among these salvianolates, magnesium lithospermate B (or magnesium salvianolate B, MLB) is the primary chemical component.

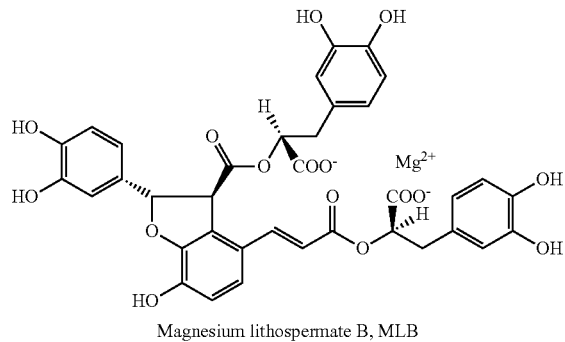

Magnesium lithospermate B, MLB

However, there has been no report on purification/separation methods for the industrial preparation of high purity magnesium lithospermate B. For example, the Chinese patent CN1911272A reported a powder injection preparation containing high purity depside salts from *Salvia miltiorrhiza* and a preparation method thereof. Nevertheless, the content of magnesium lithospermate B is only of 50-95%, and the higher the content of magnesium lithospermate B was, the lower the yield was. Namely, the industrial production costs for obtaining high purity magnesium lithospermate B will be very expensive.

In addition, no medicament using substantially pure magnesium lithospermate B (high purity above 95%) as an active component has been reported in the prior art.

Therefore, developing a simple and stable process for preparing magnesium lithospermate B in high yield is needed; particularly, it is highly needed to improve the yield while preparing high purity (>95%) magnesium lithospermate B.

SUMMARY OF INVENTION

One of the objects of the present invention is to provide a process for preparing magnesium lithospermate B, by which the yield of magnesium lithospermate B can be improved, and, particularly, high purity (e.g. above 95%) magnesium lithospermate B can be obtained in a higher yield, as compared with processes in the prior art. Specifically, the present invention provides a process for preparing magnesium lithospermate B, wherein the magnesium lithospermate B is extracted or purified from *Salvia miltiorrhiza* plant materials or *Salvia miltiorrhiza* extracts in the presence of an added magnesium salt.

Another object of the present invention is to provide a process for removing impurities accompanying with magnesium lithospermate B, wherein an aqueous solution of magnesium lithospermate B under an acidic or neutral pH condition is extracted with an organic solvent.

Another object of the present invention is to provide a pharmaceutical composition, comprising a pharmaceutically active component and a pharmaceutically acceptable carrier or excipient, wherein the pharmaceutically active component is magnesium lithospermate B with a content of more than 95% (weight), and the active component contains less than 0.5% of danshensu and a salt thereof, less than 2.0% of lithospermic acid or a salt thereof, and less than 2.0% of rosmarinic acid and or a salt thereof.

DETAILED DESCRIPTION OF THE PRESENT INVENTION

There are several processes for extracting salvianolates of *Salvia miltiorrhiza* or magnesium lithospermate B from *Salvia miltiorrhiza* plant materials in the prior art. Now, the inventors have found that the addition of magnesium salt(s) into these extraction or purification processes could significantly improve the yield of the final product magnesium lithospermate B. Therefore, the present invention provides a new process for preparing magnesium lithospermate B, wherein the magnesium lithospermate B is extracted or purified from *Salvia miltiorrhiza* plant materials or *Salvia miltiorrhiza* extracts in the presence of an added magnesium salt.

In one embodiment, the process for preparing magnesium lithospermate B according to the present invention comprises:

a) obtaining a *Salvia miltiorrhiza* liquid extract by extracting a *Salvia miltiorrhiza* plant material with a first alcohol-water solution, optionally concentrating the alcohol-water solution extraction of *Salvia miltiorrhiza* to give a concentrated *Salvia miltiorrhiza* liquid extract; and b) separating the *Salvia miltiorrhiza* liquid extract or the concentrated *Salvia miltiorrhiza* extract liquid via chromatography on macroporous absorption resin, wherein a second alcohol-water solution is used for elution, collecting the eluate containing magnesium lithospermate B;

wherein the said magnesium salt is added into at least one of the following: the first alcohol-water solution in a), the *Salvia miltiorrhiza* liquid extract or the concentrated *Salvia miltiorrhiza* liquid extract in b), and the second alcohol-water solution in b).

In another embodiment, the process for preparing magnesium lithospermate B according to the present invention comprises:

c) separating the *Salvia miltiorrhiza* extract via chromatography with macroporous absorption resin, wherein a third alcohol-water solution is used for elution, collecting the eluate containing magnesium lithospermate B, wherein the said magnesium salt(s) is/are added into said *Salvia miltiorrhiza* extract and/or the third alcohol-water solution.

The magnesium salt used for the present invention may be any kinds of magnesium salts that would not adversely affect the present invention. In a specific embodiment, the magnesium salt comprises, but not limited to, one or more of the following compounds: magnesium sulfate ($MgSO_4$), magnesium acetate ($Mg(Ac)_2$), magnesium chloride ($MgCl_2$), magnesium bromide (MgBr$_2$), magnesium carbonate (MgCO$_3$), and magnesium bicarbonate (Mg(HCO$_3$)$_2$).

The amount of the magnesium salt that is added may be 0.1-500 mg per 100 g of the *Salvia miltiorrhiza* plant material or the *Salvia miltiorrhiza* extract. In a specific embodiment, the amount of the magnesium salt(s) added is 1-300 mg per 100 g of the *Salvia miltiorrhiza* plant material or the *Salvia miltiorrhiza* extract, preferably 5-200 mg per 100 g of the *Salvia miltiorrhiza* plant material or the *Salvia miltiorrhiza* extract, more preferably 10-150 mg per 100 g of the *Salvia miltiorrhiza* plant material or the *Salvia miltiorrhiza* extract, and most preferably 50-100 mg per 100 g of the *Salvia miltiorrhiza* plant material or the *Salvia miltiorrhiza* extract.

According to the method of present invention, the first alcohol-water solution, the second alcohol-water solution and the third alcohol-water solution may be the same or different, each of which is independently selected from $C_1$-$C_4$ aqueous alcohol solutions of different concentrations of 0-80%, 5-60%, 10-50%, or 20-40%. In one specific embodiment, the first alcohol-water solution, the second alcohol-water solution, and the third alcohol-water solution are all ethanol-water solution.

The macroporous absorption resin used for the chromatography separation in the present invention comprises, but was not limited to, one or more of the following resins: HP20, HPD-80, HPD-100, HPD-100B, HPD-200A, HPD-300, HPD-450, HPD-722, HPD-826, ADS-5, ADS-8, ADS-21, D101, AB-8, 1300-I.

In an embodiment, the process according to the present invention may further comprises concentrating the magnesium lithospermate B eluate collected in the above step b) or c) to give a concentrated eluate, adjusting the pH value of the concentrated eluate to 3-7, and then extracting the same with an organic solvent to give a raffinate containing magnesium lithospermate B. Materials used for adjusting the pH value of the concentrated eluate are not specifically restricted, and may be one or more inorganic or organic acids, such as, one or more of hydrochloric acid, sulfuric acid, phosphoric acid, citric acid, trifluoroacetic acid, formic acid, and acetic acid. Organic solvents used for extraction may be selected from $C_3$-$C_6$ alcohols, $C_1$-$C_6$ alkyl $C_1$-$C_3$ carboxylates, and di($C_1$-$C_5$ alkyl)ethers. The preferred organic solvents used for extraction is selected from one or more of the following solvents: n-butyl alcohol, methyl acetate, ethyl acetate, propyl acetate, butyl acetate, methyl t-butyl ether, diethyl ether.

In an optional advantageous embodiment, the process of the present invention further comprises concentrating the raffinate containing magnesium lithospermate B, followed by alcohol-precipitating, filtrating, and drying to give a solid material containing magnesium lithospermate B. The solvents used for alcohol-precipitating may be ethanol or an aqueous ethanol solution, preferably an aqueous ethanol solution with a concentration of 85-95%.

The drying may be carried out by one or more of following methods: spray drying, vacuum drying and freeze drying.

In addition, the inventors have surprisingly found that some water-soluble phenolic acid impurities that usually accompanied with magnesium lithospermate B during the extraction and purification processes may be removed by a simple organic solvent extraction of an aqueous solution of the magnesium lithospermate B product.

Therefore, another aspect of the present invention provides a process for removing the impurities accompanying with a magnesium lithospermate B product, wherein an aqueous solution of the magnesium lithospermate B product under an acidic or neutral pH condition, preferably pH 3 to 7, is extracted by an organic solvent. The magnesium lithospermate B products are preferably obtained by extracting a *Salvia miltiorrhiza* plant material, wherein the content of the main component magnesium lithospermate B is more than or equal to 50%, preferably more than or equal to 55%, 60%, 65%, 70%, 75%, 80%, 85%, 90%, or 95%, and less than 99%, 98%, 97%, 96%, or 95%. The present invention relates to any numerical range composed by these end values. The impurities accompanied with magnesium lithospermate B herein comprise danshensu or a salt thereof, lithospermic acid or a salt thereof, and rosmarinic acid or a salt thereof, for example, sodium danshensu, potassium danshensu, sodium rosmarinate, potassium rosmarinate, dipotassium lithospermate, magnesium lithospermate, etc. These substances are homologs of magnesium lithospermate B and have very similar physical and chemical properties with magnesium lithospermate B. It is indeed unexpected that extraction by organic solvents could substantially eliminate these impurities without notable loss of magnesium lithospermate B, since they are similar in properties with magnesium lithospermate B. Organic solvents useful for the extraction are preferably selected from $C_3$-$C_6$ alcohols, $C_1$-$C_6$ alkyl $C_1$-$C_3$ carboxylates, and di($C_1$-$C_5$ alkyl)ethers. More preferably, the organic solvents useful for the extraction is selected from one or more of the following solvents: n-butyl alcohol, methyl acetate, ethyl acetate, propyl acetate, butyl acetate, methyl t-butyl ether, diethyl ether.

Another object of the present invention is to provide a high purity magnesium lithospermate B prepared by the process according to the present invention, wherein the high purity magnesium lithospermate B product comprises more than 95%, preferably more than 96%, more preferably more than 97%, and most preferably more than 98% by weight of magnesium lithospermate B. In an embodiment, the high purity magnesium lithospermate B product comprises less than or equal to 5%, preferably less than or equal to 4%, more preferably less than or equal to 3%, and most preferably less than or equal to 2% by weight impurities, said impurities comprise one or more of danshensu, lithospermic acid and rosmarinic acid.

Another aspect of the present invention provides a pharmaceutical composition, comprising a pharmaceutically active component and a pharmaceutically acceptable carrier or excipient, wherein the pharmaceutically active component is a magnesium lithospermate B product with content more than 95% by weight obtained by extraction from *Salvia miltiorrhiza* plant materials, and the magnesium lithospermate B product comprises danshensu and a salt thereof with a content being less than 0.5%, preferably less than 0.4%, less than 0.3%, less than 0.2%, less than 0.1%, or less than 0.05%; lithospermic acid and a salt thereof with a content being less than 2.0%, preferably less than 1.5%, less than 1.0%, less than 0.9%, less than 0.8%, less than 0.7%, less than 0.6%, less than 0.5%, less than 0.4%, less than 0.3, less than 0.2%, or less than 0.1%; and rosmarinic acid and a salt thereof with a content being less than 2.0%, preferably less than 1.5%, less than 1.0%, less than 0.9%, less than 0.8%, less than 0.7%, less than 0.6%, less than 0.5%, less than 0.4%, less than 0.3, less than 0.2%, or less than 0.1%. Preferably, the magnesium lithospermate B product contains danshensu and a salt thereof with a content being more than 0.01%, lithospermic acid and a salt thereof with a content being more than 0.1%, and rosmarinic acid and a salt thereof with a content being more than 0.1%. Preferably, the magnesium lithospermate B product in the pharmaceutical composition has a content of dipotassium lithospermate B of less than 0.5%, preferably less than 0.3%, and more preferably less than 0.1%. The magnesium lithospermate B product in the pharmaceutical composition may have a content of dipotassium lithospermate B of more than 0.01%, more than 0.05%, or more than 0.1%. Preferably, the magnesium lithospermate B product in the pharmaceutical composition of the present invention has a content of free lithospermic acid B of less than 1%, preferably less than 0.5%, preferably less than 0.3%, and more preferably less than 0.1%. The magnesium lithospermate B product in the pharmaceutical composition may have a content of free lithospermic acid B of more than 0.01%, more than 0.05%, or more than 0.1%. For each of the above components described by an upper limit value and a lower limit value, the present invention relates to numerical ranges composed by any one of the upper limit values and any one of the lower limit values. Most preferably, the magnesium lithospermate B in the pharmaceutical composition of the present invention is prepared by the process as described in the present invention.

Magnesium lithospermate B are useful for the treatment of cardiovascular diseases, such as coronary heart disease, angina pectoris, myocardial infarction, ischemic stroke, etc.

In the high purity magnesium lithospermate B according to the present invention, impurities such as magnesium lithospermate, sodium rosmarinate, and so on has been removed, wherein these impurities show weak biological activity and had been difficult to be removed in the prior art. Furthermore, the inventors of the present invention have also found that magnesium lithospermate B shows good stability, and displays less cardiotoxicity compared with free lithospermic acid B. Moreover, magnesium lithospermate B exhibits better activities than free acid (lithospermic acid B), other salt (dipotassium lithospermate B), and low purity mixture (depside salts of *Salvia miltiorrhiza*) in the rat tail bleeding model. Thus, the pharmaceutical composition of the present invention containing magnesium lithospermate B as the active component, wherein the homologous impurities such as magnesium lithospermate, sodium rosmarinate, etc. and/or free lithospermic acid B and other salts thereof have been substantially removed, shows superiority in terms of biological activity.

The high purity magnesium lithospermate B prepared by the process according to the present invention may be prepared as various pharmaceutical compositions. The dosage forms of the pharmaceutical compositions comprise, but not limited to, solutions, injections, tablets, sugar coated tablets, film coated tablets, enteric coated tablets, capsules, hard capsules, soft capsules, oral liquids, buccal agents, granules, electuaries, pills, powders, pastes, sublimed preparations, suspensions, suppositories, ointments, plasters, creams, sprays, drops, patches, and drop pills. The pharmaceutical composition formulated from the high purity magnesium lithospermate B prepared by the process according to the present invention may be applied to improvement of microcirculation, anti-atherosclerosis, anti-free radical oxidation damage, and similar conditions.

The methods for preparing magnesium lithospermate B according to the present invention have showed advantages since they are simple and can be carried out with low cost, and can be easily implemented in industrial scale, and can give magnesium lithospermate B with higher purity and yield. Specifically, it is discovered for the first time in the present invention that the adding of magnesium salts during the extraction and purification of magnesium lithospermate B can result in a significantly improved yield of magnesium lithospermate B (about 3%) for obtaining high purity magnesium lithospermate B (more than 95%). The yield of magnesium lithospermate B according to the present invention is increased by 20% over the prior art, especially over the process described in Chinese patent publication CN102058599A, and thereby the production efficiency is further improved. In addition to the improved yield, the present invention can result in a magnesium lithospermate B product with a higher purity (e.g. more than 95%) via a simple extraction process, while the high purity magnesium lithospermate B product otherwise can only be obtained via complicated separation. Therefore, the process according to the present invention is quite meaningful for massive industrial production, and the magnesium lithospermate B prepared by the process according to the present invention is very suitable for medicament preparation.

EXAMPLES

Figure 1:
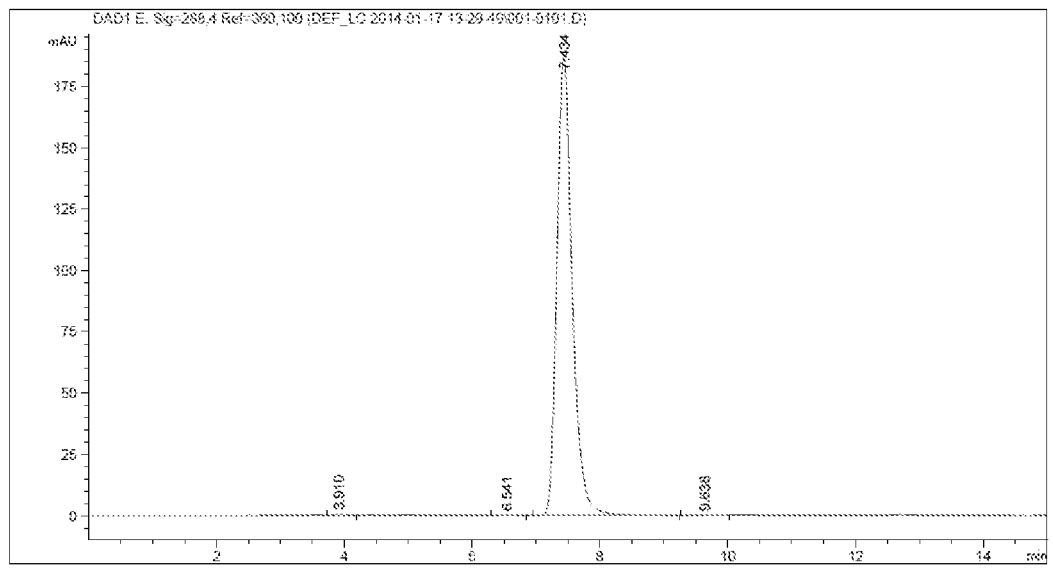
FIG. 1 is a high performance liquid chromatogram (HPLC) of lithospermic acid B control.

The following examples are used to exemplarily illustrate the present invention, but should not be understood as limiting the scope of the present invention in any way.

I. Preparation of Magnesium Lithospermate B

Example 1

1 kg *Salvia miltiorrhiza* plant material (purchased from Shanghai Traditional Chinese Medicine Co., Ltd.; lot number: 131001) was taken and smashed. The smashed *Salvia miltiorrhiza* plant material was sequentially extracted with 7 L, 5 L, and 3 L of 50% ethanol-water solution for three times (2 hours for each time) under reflux condition. The extract liquids were combined and concentrated under reduced pressure until the alcohol was completely removed. The obtained concentrated liquid was filtered to give 6 L filtrate (relative density is 1.02), which was then subjected to adsorption chromatography with 3 kg macroporous resin D101 (Tianjin Haiguang Chemical Engineering Co. Ltd.). Elution was carried out with 6 column volumes of 0% and 6% aqueous ethanol-$MgCl_2$ in sequence (the eluant 6% aqueous ethanol/magnesium chloride solution comprises 500 mg magnesium chloride in total), then 2 column volumes of 20% ethanol-water eluant, followed with 50% ethanol-water eluant until completion. The eluate comprising magnesium lithospermate B was collected and concentrated under reduced pressure until the alcohol was completely removed. Then, the pH of the concentrated magnesium lithospermate B liquid was adjusted to weak acidity. The concentrated liquid was continuously counter-flow extracted with ethyl acetate. The aqueous solution fraction was collected and concentrated until the concentration of magnesium lithospermate B was about 100 mg/ml, followed by alcohol-precipitating with 95% ethanol and filtration. The filtrate was concentrated and dried under reduced pressure to give 30.8 g magnesium lithospermate B solid, the content of magnesium lithospermate B was 96.70%, and the yield was 2.98% based on the plant material. The primary impurities were 0.76% lithospermic acid and salt(s) thereof, 0.62% rosmarinic acid and salt(s) thereof, and 0.12% danshensu and salt(s) thereof.

Example 2

1 kg Salvia miltiorrhiza plant material (purchased from Shanghai Traditional Chinese Medicine Co., Ltd.; lot number: 131001) was taken and smashed. The smashed Salvia miltiorrhiza plant material was sequentially extracted with 6 L, 5 L, and 3 L of 70% ethanol-water solution for three times (2 hours for each time) under reflux condition. The extract liquids were combined and concentrated under reduced pressure until the alcohol was completely removed. The concentrated liquid was added with 200 mg magnesium chloride under stirring condition, the liquid was then filtered and subjected to chromatography with macroporous resin HPD-100 (Bon Chemical Engineering Co. Ltd.). Elution was carried out with 6 column volumes of 0% and 6% ethanol-water solutions in sequence, and then 2 column volumes of 20% ethanol-water solution, followed by 45% ethanol-water solution until completion. The eluate comprising magnesium lithospermate B was collected and concentrated under reduced pressure until the alcohol was completely removed. The pH of the resulting concentrated magnesium lithospermate B liquid was adjusted to weak acidity. The concentrated liquid was extracted with 1-fold volume of ethyl acetate for three times. The aqueous solution fraction was collected and concentrated until the concentration of magnesium lithospermate B was about 50 mg/ml, followed by alcohol-precipitating with 90% ethanol and filtration. The filtrate was concentrated and dried under reduced pressure to give 30.6 g magnesium lithospermate B solid, and the content of magnesium lithospermate B was 96.30%, the yield was 2.95% based on the plant material. The primary impurities were 0.80% lithospermic acid and salt(s) thereof, 0.71% rosmarinic acid and salt(s) thereof, and 0.13% danshensu and salt(s) thereof.

II. Detection and Analysis of Magnesium Lithospermate B and Primary Impurities

1. Chromatographic Analysis and Detection of Magnesium Lithospermate B

Equipment: Agilent 1260 high performance liquid chromatograph, Empower2 chromatography workstation, full wavelength diode array detector; Sartorius cp225D hundred thousandth electronic balance.

Chromatographic column: YMC C18 chromatographic column (250×4.6 mm, 5 μm);

Reagents: methanol was chromatographically pure; water was ultrapure water prepared by Millipore; all the other reagents were analytically pure.

The lithospermic acid B control was purchased from National Institutes For Food And Drug Control, lot number: 111562-201212, for content determination.

Chromatographic conditions and system suitability testing: octadecylsilane bonded silica gel was used as filler; flow rate: 1.0 ml·min$^{-1}$; column temperature: 30° C.; detection wavelength: 288 nm. Theoretical plate number calculated on lithospermic acid B was no less than 5000; using methanol and 0.05% formic acid aqueous solutions as mobile phase, isocratic elution (the ratio of methanol was 45%) was performed for 30 mins.

Preparation of lithospermic acid B control solution: lithospermic acid B control was accurately weighed, moved to a volumetric flask, dissolved with water and well shaken at 25° C. ambient temperature, and diluted to scale mark.

Preparation of sample solution: a sample was accurately weighed, dissolved with water and shaken well at 25° C. ambient temperature, and diluted to scale mark.

Determination method: the control solution was accurately taken and injected into the liquid chromatograph, and the chromatogram was generated and recorded; the sample was accurately taken and injected into the liquid chromatograph, the ratio of peak areas was calculated.

The HPLC chromatogram of lithospermic acid B control is shown in FIG. 1.

Figure 2:
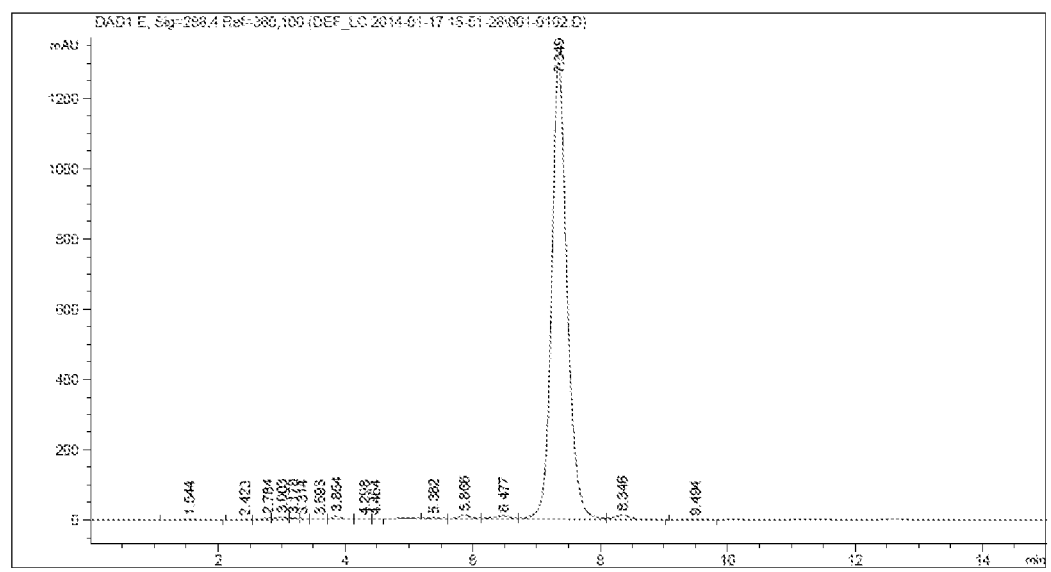
FIG. 2 is a HPLC chromatogram of the magnesium lithospermate B solid prepared according to Example 1 of the present invention.

The HPLC chromatogram of the magnesium lithospermate B solid prepared according to Example 1 of the present invention is shown in FIG. 2.

2. Detection of Metal Cations in Magnesium Lithospermate B

Equipment: DIONEX ICS900 ion chromatograph, Thermo DS5 electric conductivity detector; Inhibitor Thermo CSRS 300 4 mm; Workstation Chromeleon 7; SPE-C18 small column; Sartorius cp225D hundred thousandth electronic balance.

Chromatographic column: Dionex IonPac CS12A; Guard column: Dionex IonPac CG12A; eluted with 20 mM aqueous methylsulfonic acid solution.

Six Cation-II Standard was purchased from DIONEX Company for content determination and analysis.

Chromatographic conditions and determination method: flow rate: 1.0 ml·min$^{-1}$; injection volume: 10 μl; the sample of the magnesium lithospermate B was formulated to 1000 ppm mother liquor with deionized water, which was diluted to 100 ppm immediately before experiment; after addition of hydrochloric acid (final concentration of 20 mM), the sample was passed through SPE-C18 adsorption column at a rate of one drop per second, then passed through microporous filter membrane, and injected directly.

Six Cation-II Standard curve: Six Cation-II Standard was accurately weighed, moved to a volumetric flask, dissolved with water and well shaken at 25° C., and diluted to scale mark.

Determination method: The Six Cation-II Standard solution was accurately taken and injected into the ion chromatograph, and the chromatogram was recorded; the sample was accurately taken and injected into the ion chromatograph; the ratio of peak areas was calculated.

Figure 3:
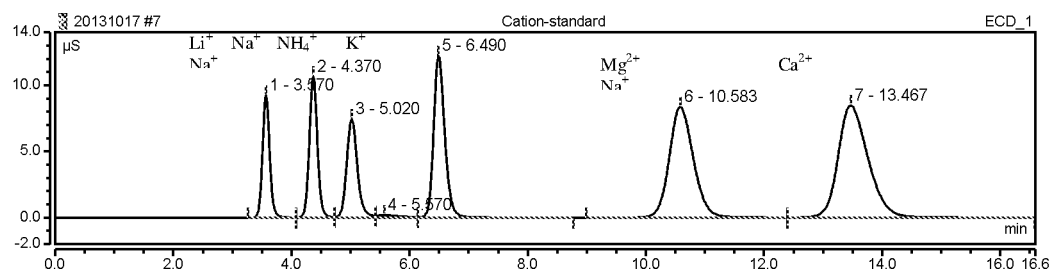
FIG. 3 is an ion chromatography of six-cation standard solution control.

The chromatogram of six-cation standard solution control was shown in FIG. 3.

Figure 4:
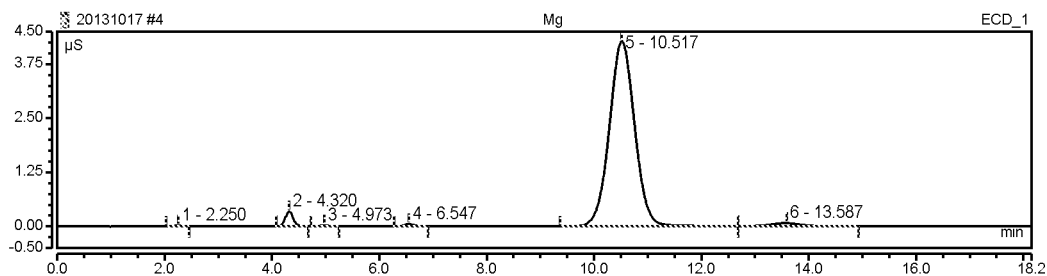
FIG. 4 is an ion chromatography of the magnesium lithospermate B prepared according to Example 6 of the present invention.

The ion chromatogram of magnesium lithospermate B prepared according to Example 6 of the present invention was shown in FIG. 4.

The experimental results showed that magnesium lithospermate B was obtained from the present invention.

3. Structure Confirmation of Magnesium Lithospermate B and Primary Impurities

Impurities were separated from the magnesium lithospermate B product of Example 1 of the present invention by gel column chromatography and C18 column, and structurally confirmed by electrospray ionization mass spectrometry (ESI-MS), nuclear magnetic resonance (NMR), and Thermo ion chromatography. The results were as follows:

3.1 Sodium Salt of Danshensu

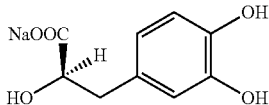

$^1$H NMR (D$_2$O, 400 MHz) δ: 6.79 (d, J=2.0 Hz, 1H), 6.67 (d, J=8.2 Hz, 1H), 6.59 (dd, J=8.2, 2.0 Hz, 1H), 5.18 (dd, J=8.4, 4.0 Hz, 1H), 3.42 (dd, J=14.3, 4.0 Hz, 1H), 3.25 (dd, J=14.3, 8.4 Hz, 1H); $^{13}$C NMR (D$_2$O, 100 MHz) δ: 174.1, 145.3, 144.1, 130.1, 121.7, 117.4, 116.3, 78.6, 39.4; ESI-MS (m/z) 221.2 [M+Na]$^+$; IC: Na$^+$.

3.2 Magnesium Salt of Lithospermic Acid

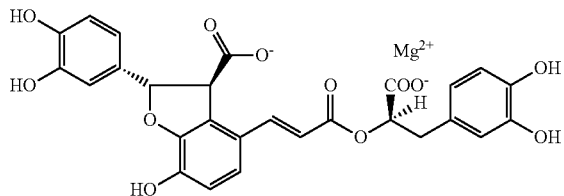

$^1$H NMR (D$_2$O, 400 MHz) δ: 7.56 (d, J=16.0 Hz, 1H), 7.03 (d, J=1.5 Hz, 1H), 6.94 (d, J=1.0 Hz, 1H), 6.93 (d, J=8.5 Hz, 1H), 6.88 (dd, J=8.5 Hz, 1H), 6.86 (d, J=8.5 Hz, 1H), 6.83 (dd, J=8.0, 1.5 Hz, 1H), 6.81 (d, J=8.5 Hz, 1H), 6.76 (dd, J=8.5, 1.0 Hz, 1H), 6.20 (d, J=16.0 Hz, 1H), 5.81 (d, J=6.0 Hz, 1H), 4.98 (dd, J=9.5, 3.5 Hz, 1H), 4.23 (d, J=5.5 Hz, 1H), 3.13 (dd, J=14.1, 3.5 Hz), 3.05 (dd, J=14.1, 9.5 Hz, 1H); $^{13}$C NMR (D$_2$O, 100 MHz) δ: 182.3, 180.1, 171.4, 149.7, 147.3, 147.0, 146.8, 145.6, 145.3, 145.1, 136.3, 133.4, 131.6, 126.5, 124.6, 124.2, 121.3, 120.4, 119.8, 119.2, 119.1, 118.7, 116.2, 91.9, 79.7, 62.3, 40.0; ESI-MS (m/z) 561.1 [M+Na]$^+$; IC: Mg$^{2+}$.

3.3 Rosmarinic Acid

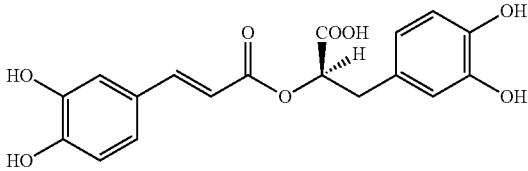 [SMILES: O=C(/C=C/c1ccc(O)c(O)c1)O[C@H](Cc1ccc(O)c(O)c1)C(=O)O]

$^1$H NMR ((CD$_3$)$_2$CO, 400 MHz) δ: 7.55 (d, J=16.0 Hz, 1H), 7.14 (d, J=2.0 Hz, 1H), 7.01 (dd, J=8.2, 2.0 Hz, 1H), 6.84 (d, J=8.2 Hz, 1H), 6.83 (dd, J=2.0 Hz, 1H), 6.68 (d, J=8.3 Hz, 1H), 6.59 (dd, J=8.3, 2.0 Hz, 1H), 6.23 (d, J=16.0 Hz, 1H), 5.17 (br.d, J=8.0 Hz, 1H), 3.07 (br.d, J=14.3 Hz, 1H), 2.93 (dd, J=14.3, 8.0 Hz, 1H); $^{13}$C NMR ((CD$_3$)$_2$CO, 100 MHz) δ: 171.1, 166.5, 148.5, 145.6, 145.4, 144.7, 143.3, 128.6, 126.7, 121.6, 120.7, 117.1, 115.3, 115.0, 114.6, 114.2, 72.6, 37.5; ESI-MS (m/z) 361.2 [M+H]$^+$.

3.4 Magnesium Lithospermate B

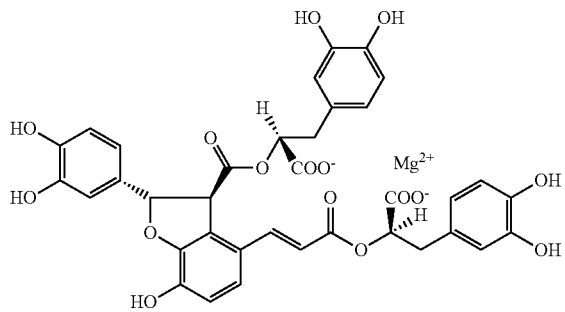

$^1$H NMR (CD$_3$OD, 500 MHz) δ: 7.52 (d, J=15.9 Hz, 1H), 7.15 (d, J=8.5 Hz, 1H), 6.83 (d, J=8.5 Hz, 1H), 6.76 (d, J=1.9 Hz, 1H), 6.74 (d, J=4.3 Hz, 1H), 6.73 (d, J=1.5 Hz, 1H), 6.69 (d, J=8.0 Hz, 1H), 6.65 (dd, J=8.2, 2.0 Hz, 1H), 6.61 (dd, J=8.2, 1.9 Hz, 1H), 6.54 (d, J=8.0 Hz, 1H), 6.51 (d, J=1.9 Hz, 1H), 6.30 (dd, J=8.1, 1.9 Hz, 1H), 6.20 (d, J=15.9 Hz, 1H), 5.85 (d, J=4.8 Hz, 1H), 5.20-5.15 (m, 2H), 4.35 (d, J=4.8 Hz, 1H), 3.06 (dd, J=14.3, 4.3 Hz, 1H), 3.03-2.96 (m, 2H), 2.83 (dd, J=14.3, 9.6 Hz, 1H); $^{13}$C NMR (CD$_3$OD, 125 MHz) δ: 171.8, 170.7, 170.4, 166.2, 147.2, 144.9, 144.7, 144.2, 144.1, 143.4, 143.2, 141.7 131.8, 127.4, 127.1, 124.5, 122.8, 120.4, 120.2, 119.9, 116.5, 116.5, 115.7, 115.4, 114.7, 114.6, 114.5, 114.5, 111.5, 86.4, 73.7, 72.8, 56.1, 36.0, 35.6; ESI-MS (m/z) 741.2 [M+Na]$^+$; IC: Mg$^{2+}$.

III. Research on Extraction or Purification Process of Magnesium Lithospermate B 1. Effect of a Magnesium Salt on the Yield of Magnesium Lithospermate B In order to investigate the effect of the added magnesium salts on the yield of magnesium lithospermate B during extraction and separation process, the following verification experiments were conducted.

Comparative Example 1 (Without Addition of Any Magnesium Salt)

100 g *Salvia miltiorrhiza* plant material (purchased from Shanghai Traditional Chinese Medicine Co., Ltd.; lot number: 131001) was taken, and divided into 50 g as one extraction unit. The extraction steps for each unit were as follows:

(1) 50 g *Salvia miltiorrhiza* plant material was extracted with 300 ml 70% ethanol under reflux for 2 hours, and filtrated, and 180 ml filtrate was collected. The residue was further added with 250 ml 70% ethanol for extraction under reflux for 2 hours and filtrated, and 235 ml filtrate was collected. The residue was further added with 250 ml 70% ethanol for extraction under reflux for 2 hours and filtrated, and 225 ml filtrate was collected. The filtrates were combined (640 ml). The ethanol was recovered, and 82 g liquid extract was obtained with a relative density of 1.091 (60° C.), which was diluted to a relative density of 1.02 with water, and filtrated to obtain 305 ml filtrate. The resulting filtrate was slowly charged into 150 g 1300-I (Yangzhou Pharmaceutical Co., Ltd.) macroporous resin adsorption column. After completion of the adsorption, 300 ml water was used to wash away sugars, proteins, and inorganic salts. Further, 300 ml 6% ethanol was used to remove other salvianolates except magnesium lithospermate B. Finally, 150 ml 20% ethanol was used for elution. Each 10 ml eluate was collected as one fraction, 120 ml volume of eluate was obtained after confirmed by HPLC detection. The eluate was concentrated under reduced pressure at vacuum degree of −0.07 to −0.1 MPa and temperature of ≤80° C. to obtain 5.7 g extract with a relative density of 1.15 (50° C.).

(2) 50 g of the rest *Salvia miltiorrhiza* plant material was extracted with 300 ml 70% ethanol under reflux for 2 hours, and filtrated, and 190 ml filtrate was collected. The residue was further added with 250 ml 70% ethanol for extraction under reflux for 2 hours and filtrated, and 225 ml filtrate was collected. The residue was further added with 250 ml 70% ethanol for extraction under reflux for 2 hours and filtrated, and 220 ml filtrate was collected. The filtrates were combined (635 ml). The ethanol was recovered, and 95 g extract paste was obtained with a relative density of 1.090 (60° C.), which was diluted to a relative density of 1.02 with water, and filtrated to obtain 305 ml filtrate. The resulting filtrate was slowly charged into 150 g 1300-I (Yangzhou Pharmaceutical Co., Ltd.) macroporous resin adsorption column. After completion of adsorption, 300 ml water was used to wash away sugars, proteins, and inorganic salts. Further, 300 ml 6% ethanol was used to remove other salvianolates except magnesium lithospermate B. Finally, 150 ml 20% ethanol was used for elution. Each 10 ml eluate was collected for one fraction, 110 ml volume of eluate was obtained after confirmed by HPLC detection. The eluate was concentrated under reduced pressure at vacuum degree of −0.07 to −0.1 MPa and temperature of ≤80° C. to obtain 5.5 g extract with a relative density of 1.15 (50° C.).

11.2 g liquid extract was obtained by combining the extracts from above units (1) and (2). After addition of 300 ml 95% ethanol, the mixture was left standing for 2 hours for alcohol precipitation, and then filtrated to give 290 ml clear liquid. The filtrate was subjected to ethanol recovery at vacuum degree of −0.07 to −0.1 MPa with temperature of ≤60° C., and then dried at vacuum degree of 0.08 MPa and temperature of ≤60° C. to give 3.27 g magnesium lithospermate B with a content of 85.10% in 2.78% yield (based on plant material).

Comparative Example 2 (With Addition of Potassium Chloride)

The process steps were the same as those of Comparative Example 1 except that potassium chloride (16 mg, 0.21 mmol) was added during the extraction process. 3.17 g of magnesium lithospermate B was obtained with a content of 84.23% in 2.67% yield (based on plant material).

Example 3

The process steps were the same as those of Comparative Example 1 except that magnesium chloride (20 mg, 0.21 mmol) was added during the extraction process. 3.86 g of magnesium lithospermate B was obtained with a content of 86.36% in 3.33% yield (based on plant material).

Example 4

The process steps were the same as those of Comparative Example 1 except that magnesium chloride (20 mg, 0.21 mmol) was added into the concentrated extract liquid. 4.07 g of magnesium lithospermate B was obtained with a content of 84.21% in 3.42% yield (based on plant material).

Example 5

The process steps were the same as those of Comparative Example 1 except that magnesium chloride (20 mg, 0.21 mmol) was added into the water-elution phase during column separation. 3.95 g of magnesium lithospermate B was obtained with a content of 85.31% in 3.37% yield (based on plant material).

Table 1 shows the purities, solid amounts, yields, and relative increasing rates of the yields of magnesium lithospermate B obtained in Comparative Examples 1-2 and Examples 3-5, wherein the relative increasing rate of the yields was calculated based on the yield of Comparative Example 1: relative increasing rate=(yield−yield of Comparative Example 1)/yield×100%.

TABLE 1

Effect of the magnesium salt (magnesium chloride) on the yield of magnesium lithospermate B

| | Added salt | Purity of magnesium litho- spermate B (%) | Amount of obtained solid (g) | Yield of magnesium litho- spermate B (%) | Relative in- creasing rate (%) |
|---|---|---|---|---|---|
| Comparative Example 1 | — | 85.10 | 3.27 | 2.78 | 0 |
| Comparative Example 2 | KCl | 84.23 | 3.17 | 2.67 | −3.96 |
| Example 3 | MgCl$_2$ | 86.36 | 3.86 | 3.33 | 19.78 |
| Example 4 | MgCl$_2$ | 84.21 | 4.07 | 3.42 | 23.02 |
| Example 5 | MgCl$_2$ | 85.31 | 3.95 | 3.37 | 21.22 |

The comparison between the results of Comparative Examples 1-2 and Examples 3-5 indicated that the addition of a magnesium salt during extraction and separation process according to the present invention resulted in significantly higher magnesium lithospermate B yields (3.33%, 3.42%, and 3.37%) than the magnesium lithospermate B yields with no magnesium salt added or when a potassium salt was added (2.78% and 2.67%).

2. Effect of Extraction on the Purity of Magnesium Lithospermate B

Comparative Example 3

100 g *Salvia miltiorrhiza* plant material (purchased from Shanghai Traditional Chinese Medicine Co., Ltd.; lot number: 131001) was smashed, decocted and sequentially extracted three times with 4-fold volume, 2-fold volume, and 2-fold volume of water, 2 hours for each time. The extract liquids were combined, cooled to room temperature, and filtrated by centrifugation. The filtrate was slowly passed through an adsorption column packed with 3-fold volume of 1300-I macroporous resin (Yangzhou Pharmaceutical Co., Ltd.). After completion of the adsorption, 6-fold volume of water was used to wash away sugars, proteins, and inorganic salts. Further, 6-fold volume of 20% ethanol was used to remove other salvianolates except magnesium lithospermate B. Finally, 3-fold volume of 50% ethanol was used to elute salvianolates of *Salvia miltiorrhiza*. Based on TLC detection, the eluate by 50% ethanol contained rich magnesium lithospermate B. It was collected and concentrated under reduced pressure to an amount of ¹⁄₁₀ weight of the plant material; subsequently, anhydrous ethanol was slowly added in an amount of ⁹⁄₁₀ weight of the plant material under stirring condition. After standing for 2 hours, the precipitate was discarded by centrifugation. The filtrate was concentrated to an amount of ¹⁄₂₀ weight of the plant material, and then added with anhydrous ethanol in an amount of ¹⁹⁄₂₀ weight of the plant material, left standing for 2 hours, and filtrated by centrifugation. The filtrate was concentrated under reduced pressure till to dry. After pulverization, 2.57 g of magnesium lithospermate B was obtained with a content of 91.16% in 2.37% yield (based on plant material). The primary impurities were 0.78% lithospermic acid and salt(s) thereof, 6.57% rosmarinic acid and salt(s) thereof, and 0.10% danshensu and salt(s) thereof.

Comparative Example 4

100 g *Salvia miltiorrhiza* plant material (purchased from Shanghai Traditional Chinese Medicine Co., Ltd.; lot number: 131001) was smashed, decocted and sequentially extracted three times at 90-100° C. with 600, 300, and 250 ml water, 2 hours for each time. The extract liquids were combined and filtrated by centrifugation. The filtrate was concentrated under reduced pressure. The concentrated liquid (250 ml) was slowly passed through an adsorption column charged with 300 ml 1300-I macroporous resin (Yangzhou Pharmaceutical Co., Ltd.). After 800 ml water was used to wash the adsorption column for removing impurities, 600 ml 50% ethanol was further used to elute salvianolates of *Salvia miltiorrhiza*. The eluate from the 50% ethanol elution was collected and concentrated under reduced pressure to 10 ml, and slowly added with 90 ml anhydrous ethanol with stirring. After standing for 2 hours, it was then centrifuged and the precipitate was discarded. The supernatant was concentrated, dried and smashed to give salvianolates with 80.56% magnesium lithospermate B. The primary impurities were 5.21% lithospermic acid and salt(s) thereof, 8.64% rosmarinic acid and salt(s) thereof, and 0.62% danshensu and salt(s) thereof.

The resulting salvianolates of *Salvia miltiorrhiza* were dissolved with water, separated via HP20 macroporous resin column. Elution was carried out with 6 column volumes of 0% and 6% aqueous ethanol solutions in sequence, 2 column volumes of 20% aqueous ethanol solution, and then 50% aqueous ethanol solution until completion. By HPLC detection, the 50% ethanol eluate comprising magnesium lithospermate B was collected and concentrated under reduced pressure until the alcohol was completely removed. The pH of the concentrated liquid was adjusted to 5, which was subjected to reverse extracted with ethyl acetate for 3 times. The magnesium lithospermate B fraction was collected and concentrated under reduced pressure until dry. 2.16 g of magnesium lithospermate B was obtained with a content of 98.67% in 2.13% yield (based on plant material). The primary impurities were 0.52% lithospermic acid and salt(s) thereof and 0.32% rosmarinic acid and salt(s) thereof.

Comparative Example 5

100 g *Salvia miltiorrhiza* plant material (purchased from Shanghai Traditional Chinese Medicine Co., Ltd.; lot number: 131001) was extracted with 6-fold volume of 60% ethanol under reflux for 2 hours. The extraction was performed for three times in total. The extract liquids were combined and concentrated under reduced pressure until the alcohol was completely removed. The concentrated liquid was separated via HP20 macroporous resin column after filtration. Elution was carried out with 6 column volumes of 0% and 6% aqueous ethanol solutions in sequence, followed with 2 column volumes of 20% ethanol aqueous solution, and then 50% ethanol aqueous solution until completion. By HPLC detection, the 50% ethanol eluate comprising magnesium lithospermate B was collected and concentrated under reduced pressure until no alcohol smell was detected. The pH of the concentrated liquid was adjusted to 5, which was subjected to reverse extracted with ethyl acetate for 3 times. The magnesium lithospermate B fraction was collected and concentrated under reduced pressure until dry. 2.41 g of magnesium lithospermate B was obtained with a content of 96.21% in 2.32% yield (based on plant material). The primary impurities were 1.08% lithospermic acid and salt(s) thereof and 0.96% rosmarinic acid and salt(s) thereof.

Comparative Example 6

100 g *Salvia miltiorrhiza* plant material (purchased from Shanghai Traditional Chinese Medicine Co., Ltd.; lot number: 131001) was extracted with 6-fold volume of 60% ethanol under reflux for 2 hours. The extraction was performed three times in total. The extract liquids were combined and concentrated under reduced pressure until no alcohol smell was detected. The concentrated liquid was added with magnesium chloride (16 mg, 0.21 mmol) and stirred for half an hour, then separated via HP20 macroporous resin column after filtration. Elution was carried out with 6 column volumes of 0% and 6% aqueous ethanol solutions in sequence, followed with 2 column volumes of 20% ethanol aqueous solution, and then 50% ethanol aqueous solution until completion. By HPLC detection, the 50% ethanol eluate containing magnesium lithospermate B was collected and concentrated under reduced pressure until no alcohol smell was detected. The pH of the concentrated liquid was adjusted to 5, which was subjected to reverse extracted with ethyl acetate for 3 times. The magnesium lithospermate B fraction was collected and concentrated under reduced pressure until to dry. 2.97 g of magnesium lithospermate B was obtained with a content of 96.92% in 2.88% yield (based on plant material). The primary impurities were 0.92% lithospermic acid and salt(s) thereof and 0.81% rosmarinic acid and salt(s) thereof.

Table 2 shows the purities, solid amounts, yields, and relative increasing rates of the yields of magnesium lithospermate B obtained in Comparative Examples 3-5 and Example 6, wherein the relative increasing rate of the yields was calculated based on the yield of Comparative Example 3: relative increasing rate=(yield−yield of Comparative Example 3)/yield×100%.

TABLE 2

Effect of extraction process on the purity of magnesium lithospermate B

| | Extraction | Added salt | Purity of magnesium lithospermate B (%) | Amount of obtained solid (g) | Yield of magnesium lithospermate B (%) | Relative increasing rate (%) |
|---|---|---|---|---|---|---|
| Comparative Example 3 | No | — | 91.16 | 2.60 | 2.37 | 0 |
| Comparative Example 4 | Yes | — | 98.67 | 2.16 | 2.13 | −10.12 |

TABLE 2-continued

Effect of extraction process on the purity of magnesium lithospermate B

| | Extraction | Added salt | Purity of magnesium lithospermate B (%) | Amount of obtained solid (g) | Yield of magnesium lithospermate B (%) | Relative increasing rate (%) |
|---|---|---|---|---|---|---|
| Comparative Example 5 | Yes | — | 96.21 | 2.41 | 2.32 | −2.11 |
| Example 6 | Yes | MgCl$_2$ | 96.92 | 2.97 | 2.88 | 21.52 |

By comparing the results of Comparative Examples 3-5 and Example 6, it was found that the magnesium lithospermate B contents (reaching above 95%) could be significantly improved by reverse extraction. In addition, by comparing the results of Comparative Examples 4-5 and Example 6, it was further found that the yield of high purity magnesium lithospermate B could be significantly improved by the added magnesium salts. Meanwhile, the result of Comparative Example 6 showed that the content of magnesium lithospermate B could reach 98% when using despite salts of *Salvia miltiorrhiza* with purity of about 80% as raw materials.

3. Effect of the Addition Amount of a Magnesium Salt on the Yield and Purity of Magnesium Lithospermate B

Example 7

100 g *Salvia miltiorrhiza* plant material (purchased from Shanghai Traditional Chinese Medicine Co., Ltd.; lot number: 131001) was extracted with 6-fold volume of 60% ethanol under reflux condition for 2 hours. The extraction was performed for three times in total. The extract liquids were combined and concentrated under reduced pressure until no alcohol smell was detected. The concentrated liquid was added with 5 mg magnesium chloride and stirred for half an hour, and then separated via HP20 macroporous resin (Mitsubishi Chemical, Japan) column after filtration, and eluted with 6 column volumes of water, 20% ethanol, and 40% ethanol in sequence. By HPLC detection, the 40% eluate containing magnesium lithospermate B was collected and concentrated under reduced pressure until no alcohol smell was detected. The pH of the concentrated liquid was adjusted to 5, which was subjected to reverse extraction with ethyl acetate for 3 times. The magnesium lithospermate B fraction was collected and concentrated under reduced pressure until dry. 2.62 g of magnesium lithospermate B was obtained with a content of 96.63% in 2.52% yield (based on plant material).

Example 8

The process steps were the same as those of Example 5 except that 10 mg magnesium chloride was added into the concentrated extract liquid. 2.91 g of magnesium lithospermate B was obtained with a content of 95.35% in 2.77% yield (based on plant material).

Example 9

The process steps were the same as those of Example 5 except that 20 mg magnesium chloride was added into the concentrated extract liquid. 3.05 g of magnesium lithospermate B was obtained with a content of 96.81% in 2.95% yield (based on plant material).

Example 10

The process steps were the same as those of Example 5 except that 50 mg magnesium chloride was added into the concentrated extract liquid. 3.25 g of magnesium lithospermate B was obtained with a content of 94.11% in 3.06% yield (based on plant material).

Example 11

The process steps were the same as those of Example 5 except that 100 mg magnesium chloride was added into the concentrated extract liquid. 3.52 g of magnesium lithospermate B was obtained with a content of 92.56% in 3.26% yield (based on plant material).

Example 12

The process steps were the same as those of Example 5 except that 200 mg magnesium chloride was added into the concentrated extract liquid. 3.48 g of magnesium lithospermate B was obtained with a content of 93.17% in 3.24% yield (based on plant material).

Table 3 showed the purity, solid amount, and yield of magnesium lithospermate B obtained in each of Examples 7-12.

TABLE 3

Effect of the addition amount of the magnesium salt (magnesium chloride) on the yield and purity of magnesium lithospermate B

| | Addition amount of MgCl$_2$ (mg) | Amount of obtained solid (g) | Purity of magnesium lithospermate B (%) | Yield of magnesium lithospermate B (%) |
|---|---|---|---|---|
| Comparative 5 | 0 | 2.41 | 96.21 | 2.32 |
| Example 7 | 5 | 2.62 | 96.63 | 2.53 |
| Example 8 | 10 | 2.91 | 95.35 | 2.77 |
| Example 9 | 20 | 3.05 | 96.81 | 2.95 |
| Example 10 | 50 | 3.25 | 94.11 | 3.06 |
| Example 11 | 100 | 3.52 | 92.56 | 3.26 |
| Example 12 | 200 | 3.48 | 93.17 | 3.24 |

As shown in Table 3, when the added magnesium chloride at the range of 5-100 mg per 100 g *Salvia miltiorrhiza*, the more the amount of the added magnesium chloride was, the higher the magnesium lithospermate B yield was. But the magnesium lithospermate B yield was no more significantly increased when the amount of magnesium chloride was increased to 200 mg.

4. Research on Stability of Magnesium Lithospermate B

The chemical stability of magnesium lithospermate B was investigated by detecting the variation of peak areas (HPLC). Specific experimental method: lithospermic acid B (lab-made; lot number: 20131017) and magnesium lithospermate B prepared in Example 1 of the present invention were respectively formulated to 1 mg/mL aqueous solution at 25° C., which was then diluted 10 times. The variation of peak areas of lithospermic acid B at 288 nm for durations of 0, 2, 4, 6, 8, 12, and 24 hours were detected by HPLC, respectively. 10 microliters was injected for each time. The results are shown in Table 4.

Observation indicator and observation time: the observation indicator is the level of lactic dehydrogenase in cells; cell survival rate was represented by intracellular LDH content ratio, i.e. (absorbance of treated sample well–absorbance of sample control well)/(absorbance of cells with maximum enzymatic activity–absorbance of sample control well)×100.

TABLE 4

Chemical stability of magnesium lithospermate B

| Component | 0 h peak area | 2 h peak area | 4 h peak area | 6 h peak area | 8 h peak area | 12 h peak area | 24 h peak area | Average peak area | RSD (%) |
|---|---|---|---|---|---|---|---|---|---|
| Lithospermic acid B | 3957 | 3991 | 3992 | 3983 | 4002 | 3990 | 4000 | 3987.8 | 0.26 |
| Magnesium lithospermate B | 3611 | 3632 | 3614 | 3636 | 3629 | 3628 | 3599 | 3621.3 | 0.31 |

The experimental results showed that the peak areas did not significantly vary within 24 hours for each component. This illustrated the magnesium lithospermate B prepared according to Example 1 of the present invention had good chemical stability.

IV. Research of Pharmacological Activity of Magnesium Lithospermate B

Experimental Example 1. Research on Cytotoxicity and Antioxidant Activity of Lithospermic Acid B and the Magnesium Lithospermate B 1.1 Research Material and Method of Cytotoxicity Experiment 1.1.1. Materials for Cytotoxicity Experiment Sample and control: magnesium lithospermate B (prepared according to Example 6 of the present application), lithospermic acid B (lab made; lot number: 20131017), formulated with normal saline prior to use; normal saline as solvent control was derived from Jiangsu Yabang Pharmaceutical Co., Ltd.; the other reagents were all commercially available analytically pure products.

Cell lines and reagents: cardiac myoblast (H9C2); Microvascular Endothelial Cell (HMEC-1); Lactic Dehydrogenase Cytotoxicity Detection Kit, Beyotime Biotechnology Institute.

Primary equipment: multifunctional ELISA reader (Spectra MAX M2e), a product from Molecular Devices, USA; microscope (Optiphot-2), Nikon, Japan; $CO_2$ incubator, Thermo, USA; biosafety cabinet, Boxun, Shanghai.

1.1.2 Method of Cytotoxicity Experiment

Dosage setting: the dosages of lithospermic acid B and magnesium lithospermate B were set at 10, 50, 100, 200, 400, 800, 1200, 1600 μM and the incubation time was set as 24 hours in the present experiment.

Experimental method: H9C2 cells and HMEC-1 cells were respectively incubated in 10% FBS containing low saccharide DMEM medium and MCDB-131 medium, at 37° C. and 5% $CO_2$. Cells were seeded in a 96-well culture plate, which was added with different concentrations of lithospermic acid B solutions and magnesium lithospermate B solutions on the next day (about 80% fusion). After incubation for 24 hours in total, the detection was conducted according to instructions of the Lactic Dehydrogenase Cytotoxicity Detection Kit.

Statistical method: the data was presented with average±standard derivation (mean±SD); the comparison of two groups of data was statistically analyzed by student-t test method, P<0.05 indicating statistical difference.

1.1.3 Results of Cytotoxicity Experiment

Figure 5:
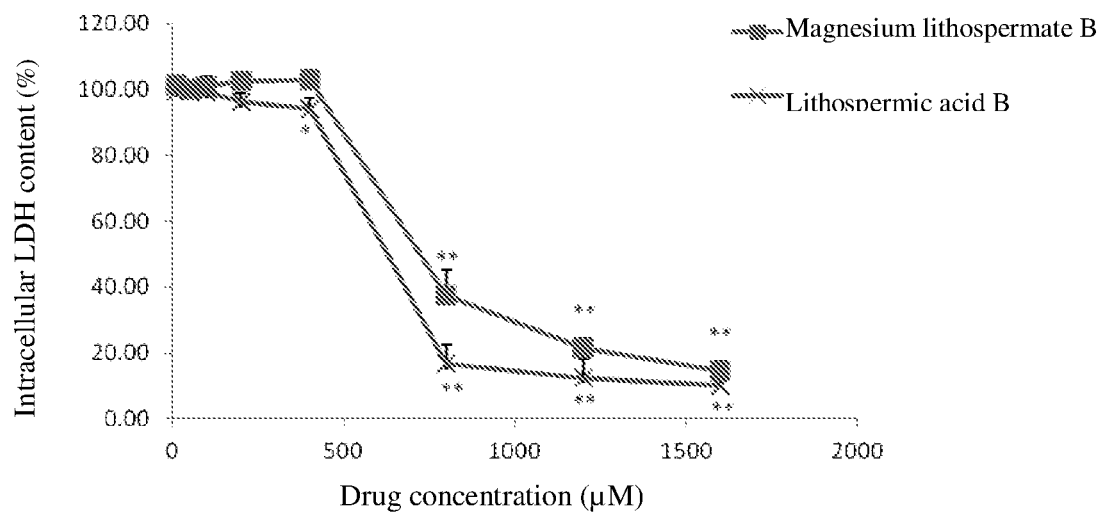
FIG. 5 shows the toxic effects of lithospermic acid B and magnesium lithospermate B to cardiac myoblast cell H9C2 (triplicate wells, n=3)
Figure 6:
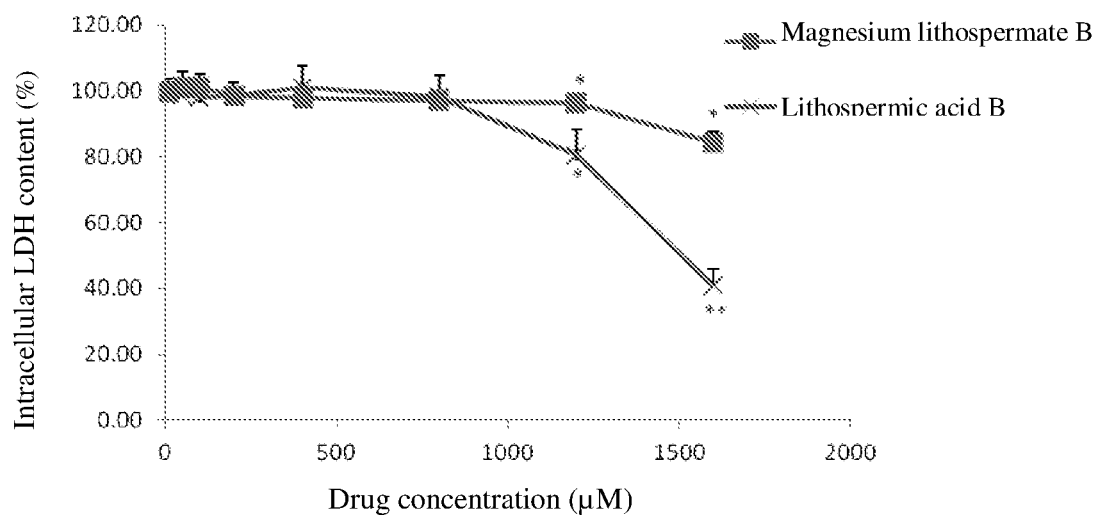
FIG. 6 shows the toxic effects of lithospermic acid B and magnesium lithospermate B to endothelial cell HMEC-1 (triplicate wells, n=3).

Different concentrations of lithospermic acid B and a magnesium lithospermate B were incubated with the cells for 24 hours. The results of intracellular LDH content detection showed that for cardiac myoblast cells H9C2, 400, 800, 1200, 1600 μM of lithospermic acid B and 800, 1200, 1600 μM of magnesium lithospermate B significantly decreased the intracellular LDH content as compared with normal control wells (P<0.05 or P<0.01); for endothelial cells HMEC-1, 1200 and 1600 μM of lithospermic acid B and 1200 and 1600 μM of magnesium lithospermate B significantly decreased the intracellular LDH content as compared with normal control wells (P<0.05 or P<0.01). See Table 5, FIG. 5, and FIG. 6.

TABLE 5

Effect of lithospermic acid B and magnesium lithospermate B on intracellular LDH content (triplicate wells, n = 3)

| | | Intracellular LDH content percent (%) | |
|---|---|---|---|
| Drug name | Dosage (μM) | H9C2 cell | HMEC-1 cell |
| Lithospermic acid B | 10 | 99.62 ± 1.67 | 99.89 ± 2.66 |
| | 50 | 99.46 ± 0.96 | 98.91 ± 1.64 |
| | 100 | 99.29 ± 2.47 | 98.21 ± 5.59 |
| | 200 | 96.18 ± 2.88 | 98.34 ± 4.26 |
| | 400 | 94.27 ± 3.31* | 100.94 ± 6.55 |
| | 800 | 16.79 ± 5.74** | 98.33 ± 6.35 |
| | 1200 | 12.47 ± 5.72** | 80.65 ± 7.61* |
| | 1600 | 10.1 ± 5.88** | 40.93 ± 5.21** |
| Magnesium lithospermate B | 10 | 101.42 ± 2.00 | 99.70 ± 3.88 |
| | 50 | 99.97 ± 1.43 | 101.05 ± 4.77 |
| | 100 | 101.25 ± 2.79 | 100.96 ± 4.01 |
| | 200 | 102.39 ± 1.37 | 98.58 ± 0.24 |
| | 400 | 102.75 ± 3.07 | 97.8 ± 1.03 |
| | 800 | 37.72 ± 7.52** | 96.93 ± 1.37 |
| | 1200 | 21.59 ± 2.86** | 96.17 ± 1.00* |
| | 1600 | 14.59 ± 3.05** | 84.28 ± 3.28* |

*P < 0.05,
**P < 0.01 vs. normal control group

Conclusion: high dosages of lithospermic acid B and magnesium lithospermate B had toxic effect on both cardiac myoblasts and endothelial cells but magnesium lithospermate B showed lower toxicity than lithospermic acid B, especially on endothelial cell line.

1.2 Research Materials and Method of in Vitro Anti-Lipid Peroxidation Experiment 1.2.1 Materials for in Vitro Anti-Lipid Peroxidation Experiment Sample and control: magnesium lithospermate B (prepared according to Example 6 of the present application), lithospermic acid B (lab-made; lot number: 20131017), formulated with normal saline prior to use; normal saline as solvent control was from Jiangsu Yabang Pharmaceutical Co., Ltd.; the other reagents were all commercially available analytically pure products. Tris base, potassium chloride, dipotassium phosphate, glycerol, etc. (Sinopharm Chemical Reagent Co., Ltd.); Coomassie brilliant blue G-250, bovine serum albumin (Shanghai Lanji Technology Development Co., Ltd.).

Experimental animal: species and strain: SD rat; source: Shanghai SLAC Laboratory Animal Co., Ltd., Laboratory Animal Production License: SCXK (Shanghai) 2012-0002; number and gender: 2, male; animal weight: 200-250 g.

1.2.2 Method of in Vitro Anti-Lipid Peroxidation Experiment

Steps for preparing liver microsome: liver tissue was taken out, cut into pieces, washed with Buffer A, wiped up, and weighed for 8 g. By adding 10 ml Buffer A per gram of tissue, 80 ml was added in total, followed by automatic homogenization and further homogenization with manual homogenizer. The homogenate was centrifuged at 10,000 g and 4° C. for 30 mins, and the supernatant was taken out. The supernatant was centrifuged at 105,000 g and 4° C. for 60 mins. The resulting precipitate is the microsome, which was then added with Buffer B to obtain microsome suspension, aliquoted into 2 ml small tubes, and stored in −70° C. refrigerator for further use. Determination of protein content: using Bradford method (Coomassie brilliant blue G-250 method).

Determination of lipid oxidation in rat liver microsome: 1 ml liver microsome was added into each tube, followed by addition of different concentrations of reagent solutions. The mixtures were well shaken and incubated in 37° C. water bath for 90 mins. After the tubes were taken out, 1 ml 10% trichloroacetic acid (TCA) and 1 ml 0.67% thiobarbituric acid (TBA) were added into each tube. The tubes were placed in boiling water bath for 15 mins, then cooled with running water and centrifuged at 3000 rpm for 10 mins. The supernatants were taken for colorimetric determination at 532 nm. The contents were calculated with standard tetraethoxypropane and represented with content per mg protein.

Calculation formula:

MDA content (nmol/mg prot)=$\{[(A_{sample}-A_{blank})\div(A_{standard}-A_{blank})]\times 10 \text{ nmol/ml}\}\div$protein content Inhibition rate %=(MDA$_{blank}$−MDA$_{sample}$)/MDA$_{blank}$×100%

1.2.2 Experimental Results

The results are shown in Table 1. At a drug concentration of 100 μM, lithospermic acid B and magnesium lithospermate B exhibited considerable anti-lipid peroxidation effects, where the inhibition rate reached around 85%, indicating that the anti-oxidation of these compounds depended on phenolic hydroxy in the chemical structures, while the salt form had no impact in this regard.

TABLE 6

In vitro antioxidant activity of lithospermic acid B and magnesium lithospermate B (n = 3)

| Compound | Inhibition rate (%) |
|---|---|
| Lithospermic acid B 100 μM | 86.42 |
| Magnesium lithospermate B 100 μM | 84.41 |

Experimental Example 2. Effects of Lithospermic Acid B, Dipotassium Lithospermate B, Depside Salts of *Salvia Miltiorrhiza*, and Magnesium Lithospermate B on Bleeding of Severed Tails of Rats 2.1 Materials and Method 2.1.1 Experimental Material Sample and control: lithospermic acid B, dipotassium lithospermate B, depside salts of *Salvia miltiorrhiza* (comprising 85% magnesium lithospermate B), magnesium lithospermate B, formulated with normal saline prior to use; normal saline as solvent control was from Jiangsu Yabang Pharmaceutical Co., Ltd.; the other reagents were all commercially available analytically pure products.

Experimental animal: species and strain: SD rat; source: Shanghai SLAC Laboratory Animal Co., Ltd., Laboratory Animal Production License: SCXK (Shanghai) 2012-0002; number and gender: 50, male; animal weight: 120-200 g.

Primary devices: water bath, scalpel, timer 2.1.2 Experimental Method

Dosage setting: the dosages of lithospermic acid type reagents were set as 50 and 100 mg/kg in the present experiment; normal saline was given as additional solvent control. Tail severing time was 2 mins after administration.

Administration route and administration dosage of sample and control: administration by injection through femoral vein, 2 ml/kg.

Experimental method: the animals were water fasted overnight. 50 mg/kg pentobarbital sodium was intraperitoneally injected for anesthesia prior to the experiment. After anesthesia of the animals, markers were made at 4 mm from tips of rat tails with a marker pen and ruler. Drugs were injected through femoral veins of the animals. 2 mins later, the tails were swiftly severed at marked positions of the animal tails with a scalpel. The remained animal tails were rapidly inserted into prepared normal saline tubes in 37° C. water bath, and timing was started. The bleeding of the animal tails was observed. If no more bleeding was observed within 30 seconds, the time was recorded as coagulation time (unit: second) of the animals. The experiment was stopped when no bleeding was observed in 30 mins, which was recorded as 1800 seconds.

Observation indicator and observation time: the indicator was the bleeding time.

Statistical method: the experimental data was represented with x±SD; GraphPad Prism 5 1 way ANOVA was applied for significance test.

2.2 Experimental Results

As shown in Table 4-1, by administrating 50 and 100 mg/kg of lithospermic acid type compounds to SD rats via intravenous injection, the bleeding time of severed tails of rats can be significantly extended; by administrating the same dosage of lithospermic acid B or the magnesium lithospermate B to SD rats via intravenous injection, the bleeding time of severed tails of rats in magnesium lithospermate B administration group was remarkably longer than lithospermic acid B administration group. In addition, at the same dosage, the bleeding time of severed tails of rats in magnesium lithospermate B administration group was significantly longer than dipotassium lithospermate B and depside salts of *Salvia miltiorrhiza* (obtained according to the description in paragraph 1 of Comparative Example 4; comprising 80.56% magnesium lithospermate B).

TABLE 7

Effect of administration of lithospermic acid B type compounds via intravenous injection on the bleeding time of severed tails of rats

| Drug name | Dosage | Animal number | Bleeding time (second) |
|---|---|---|---|
| Solvent control | 2 ml/kg normal saline | 21 | 360 ± 24 |
| Lithospermic acid B | 50 mg/kg | 10 | 869 ± 71**## |
|  | 100 mg/kg | 10 | 1078 ± 137**## |
| Magnesium lithospermate B | 50 mg/kg | 26 | 1098 ± 84** |
|  | 100 mg/kg | 10 | 1800 ± 0** |
| Dipotassium lithospermate B | 50 mg/kg | 10 | 827 ± 70**$$ |
|  | 100 mg/kg | 10 | 1301 ± 189**$$ |
| Depside salts of *Salvia miltiorrhiza* | 50 mg/kg | 10 | 1001 ± 151**$$ |

*$P < 0.05$,
**$P < 0.01$ vs. solvent control;
$P < 0.05$,
$P < 0.01$ lithospermic acid B vs. magnesium lithospermate B in the groups of the same dosage;
$$P < 0.05$,
$$$P < 0.01$ dipotassium lithospermate B or depside salts of *Salvia miltiorrhiza* vs. magnesium lithospermate B in the groups of the same dosage.

The above pharmacological experiment results indicated that magnesium lithospermate B exhibited lower toxicity than lithospermic acid B in the cytotoxicity experiments of cardiac myoblast cell H9C2 and endothelial cell HMEC-1; in addition, magnesium lithospermate B exhibited an activity superior to the free acid (lithospermic acid B), other salts (dipotassium lithospermate B), and low purity mixtures (salvianolates of *Salvia miltiorrhiza*) in the experiment for extending the bleeding time of rat tails.

We claim:

1. A process for preparing magnesium lithospermate B, comprising:
   a) obtaining a *Salvia miltiorrhiza* liquid extract by extracting a *Salvia miltiorrhiza* plant material with a first alcohol-water solution, and
   b) separating the *Salvia miltiorrhiza* liquid extract via chromatography on macroporous absorption resin, wherein a second alcohol-water solution and a third alcohol-water solution is used for elution, collecting an eluate containing magnesium lithospermate B; concentrating the eluate to give a concentrated eluate, adjusting the pH value of the concentrated eluate to 3-7, and then extracting with an organic solvent to give a raffinate comprising magnesium lithospermate B;
   wherein a magnesium salt is added into at least one of the following: the first alcohol-water solution in a), the *Salvia miltiorrhiza* liquid extract in b), the second alcohol-water solution in b), or the third alcohol-water solution in b).

2. The process according to claim 1, wherein the magnesium salt is one or more of the following compounds: $MgSO_4$, $Mg(Ac)_2$, $MgCl_2$, $MgBr_2$, $MgCO_3$, and $Mg(HCO_3)_2$.

3. The process according to claim 1 or 2, wherein the amount of the added magnesium salt is 5-200 mg per 100 g of the *Salvia miltiorrhiza* plant material or the *Salvia miltiorrhiza* extract.

4. The process according to claim 3, wherein the organic solvent is selected from $C_3$-$C_6$ alcohols, $C_1$-$C_6$ alkyl $C_1$-$C_3$ carboxylates, and di($C_1$-$C_5$ alkyl)ethers.

5. The process according to claim 4, wherein the organic solvent is one or more selected from the following solvents: n-butyl alcohol, methyl acetate, ethyl acetate, propyl acetate, butyl acetate, methyl t-butyl ether, and diethyl ether.

6. The process according to claim 4 or 5, further comprising concentrating the raffinate comprising magnesium lithospermate B, follow by alcohol-precipitating, filtrating, and drying to give a magnesium lithospermate B solid.

7. The process according to claim 6, wherein the solvent used for alcohol-precipitating is ethanol or an aqueous ethanol solution.

8. The process according to claim 1, wherein the first alcohol-water solution and the second alcohol-water solution are the same or different, and are independently selected from aqueous solutions of $C_1$-$C_4$ alcohol with a concentration of 0-80%.

9. The process according to claim 1, wherein the third alcohol-water solution is selected from aqueous solutions of $C_1$-$C_4$ alcohol with a concentration of 0-80%.

10. The process according to claim 1, further comprising concentrating the *Salvia miltiorrhiza* liquid extract to give a concentrated *Salvia miltiorrhiza* liquid extract.

11. The process according to any one of claims 1, 2, 3, 4-9, and 10, wherein the macroporous resin comprises one or more of the following resins: HP20, HPD-80, HPD-100, HPD-100B, HPD-200A, HPD-300, HPD-450, HPD-722, HPD-826, ADS-5, ADS-8, ADS-21, D101, AB-8, and 1300-I.

* * * * *